US00PP25316P2

(12) United States Plant Patent
Heuger

(10) Patent No.: US PP25,316 P2
(45) Date of Patent: Feb. 24, 2015

(54) ***HELLEBORUS* PLANT NAMED 'COSEH 1000'**

(50) Latin Name: *Helleborus niger*
Varietal Denomination: COSEH 1000

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 130 days.

(21) Appl. No.: 13/815,555

(22) Filed: Mar. 8, 2013

(51) Int. Cl.
*A01H 5/00* (2006.01)

(52) U.S. Cl.
USPC ..... Plt./439

(58) Field of Classification Search
CPC ..... A01H 5/00
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 1000', characterized by its upright and mounding plant habit; uniform and freely flowering habit; dark green-colored leaves; freely flowering habit; single white-colored flowers; and good garden performance.

2 Drawing Sheets

Botanical designation: *Helleborus niger.*
Cultivar denomination: 'COSEH 1000'.

BACKGROUND OF THE INVENTION

The present invention relates to a new and distinct cultivar of *Helleborus* plant, botanically known as *Helleborus niger* and hereinafter referred to by the name 'COSEH 1000'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in November, 2006 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in November, 2008.

Asexual reproduction of the new *Helleborus* plant by divisions in a controlled greenhouse environment in Glandorf, Germany since March, 2009 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 1000'. These characteristics in combination distinguish 'COSEH 1000' as a new and distinct *Helleborus* plant:

1. Upright and mounding plant habit.
2. Uniform and freely flowering habit.
3. Dark green-colored leaves.

4. Freely flowering habit.
5. Single white-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger* 'COSEH 230', disclosed in U.S. Plant Pat. No. 21,242. In side-by-side comparisons conducted in Glandorf, Germany, plants of the new *Helleborus* differed primarily from plants of 'COSEH 230' in the following characteristics:

1. Plants of the new *Helleborus* flowered in November/December whereas plants of 'COSEH 230' flowered in January/February.
2. Plants of the new *Helleborus* had single-type flowers whereas plants of 'COSEH 230' had semi-double-type flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 1000' grown in a container.

The photograph on the second sheet is a close-up view of a typical flowering plant of 'COSEH 1000'.

DETAILED BOTANICAL DESCRIPTION

The aforementioned photographs and following observations, measurements and values describe plants grown during the late autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger* 'COSEH 1000'.

Parentage:

*Female, or seed, parent*.—Unnamed proprietary seedling selection of *Helleborus niger*, not patented.

*Male, or pollen, parent*.—Unnamed proprietary seedling selection of *Helleborus niger*, not patented.

Propagation:

*Type*.—By tissue culture.

*Time to initiate roots, winter*.—About two months at temperatures about 12° C.

*Time to produce a rooted young plant, winter*.—About six months at temperatures about 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; moderately vigorous growth habit.

*Plant height*.—About 25.1 cm.

*Plant diameter* (*area of spread*).—About 33.6 cm.

Foliage description:

*Arrangement*.—Leaves arranged in a basal rosette; leaves palmately compound with seven leaflets per leaf.

*Leaf length*.—About 13.3 cm.

*Leaf width*.—About 15.3 cm.

*Leaflet length*.—About 8 cm.

*Leaflet width*.—About 3.6 cm.

*Leaf shape*.—Palmate; orbicular in outline.

*Leaflet shape*.—Ovate to narrowly ovate to elliptic.

*Leaflet apex*.—Acute.

*Leaflet base*.—Cuneate.

*Leaflet margin*.—Serrate.

*Leaflet texture, upper and lower surfaces*.—Smooth, glabrous; leathery.

*Leaflet venation pattern*.—Pinnate.

*Leaflet color*.—Developing leaves, upper surface: Close to 137B. Developing leaves, lower surface: Close to 138B. Fully developed leaves, upper surface: Darker than between 137A and 147A; venation, close to 144B to 144C, at the base, tinged with close to 200C. Fully developed leaves, lower surface: Close to 147B; venation, close to 145B to 145C.

*Petioles*.—Length: About 12.1 cm. Diameter: About 6 mm. Texture, upper and lower surfaces: Smooth, glabrous. Color, upper and lower surfaces: Close to 145A to 145B, slightly dotted with close to 187D.

Flower description:

*Flower shape and habit*.—Single rotate flowers arranged singly or in pairs; freely and uniform flowering habit with about 36 flowers and flower buds developing per plant; flowers facing outwardly to slightly upright.

*Fragrance*.—None detected.

*Natural flowering season*.—Plants begin flowering about ten months after planting; plants flower from late autumn into the winter in Germany.

*Flower longevity on the plant*.—About ten days; flowers not persistent.

*Flower buds*.—Length: About 2.4 cm. Diameter: About 1.2 cm. Shape: Ovate. Color: Close to 155A; towards the base, close to 157D.

*Flower diameter*.—About 8.2 cm.

*Flower depth* (*height*).—About 2.6 cm.

*Petals*.—Transformed into nectaries.

*Sepals*.—Quantity and arrangement: Five, arranged in a single whorl. Length: About 4.4 cm. Width: About 3.8 cm. Shape: Broadly ovate. Apex: Obtuse. Base: Broadly cuneate. Margin: Entire. Texture, upper and lower surfaces: Smooth, glabrous. Color: When opening, upper surface: Close to NN155D. When opening, lower surface: Close to NN155C. Fully opened, upper and lower surfaces: Close to NN155C; color becoming closer to 145C with development.

*Peduncles*.—Length: About 20.1 cm. Diameter: About 5 mm to 6 mm. Aspect: About 15° from vertical. Strength: Strong. Texture: Smooth, glabrous. Color: Close to 145C, slightly dotted with close to 187D.

*Pedicels*.—Length: About 5.1 cm. Diameter: About 3 mm. Aspect: About 40° from peduncle axis. Strength: Moderately strong. Texture: Smooth, glabrous. Color: Close to 145C to 145D; towards the base, slightly dotted with close to 187D.

*Reproductive organs*.—Stamens: Quantity per flower: About 100. Filament length: About 1.4 cm. Filament color: Close to NN155D. Anther shape: Reniform. Anther length: About 2 mm. Anther color: Close to 3B. Pollen amount: Abundant. Pollen color: Close to 2D. Pistils: Quantity per flower: About 14. Pistil length: About 9 mm. Stigma shape: Club-shaped. Stigma color: Close to NN155B. Style length: About 8 mm. Style color: Close to NN155D. Ovary color: Close to 157C. Nectaries (transformed petals): Quantity per flower: About 18. Length: About 1.1 cm. Diameter: About 3 mm. Shape: Narrow triangular, flattened tubular. Color, immature, inner and outer surfaces: Close to 144B; towards the apex, close to 144C. Color, mature, inner and outer surfaces: Close to N144A; towards the apex, close to 153D and 12A; with development, color becomes closer to 153D.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 1000' as illustrated and described.

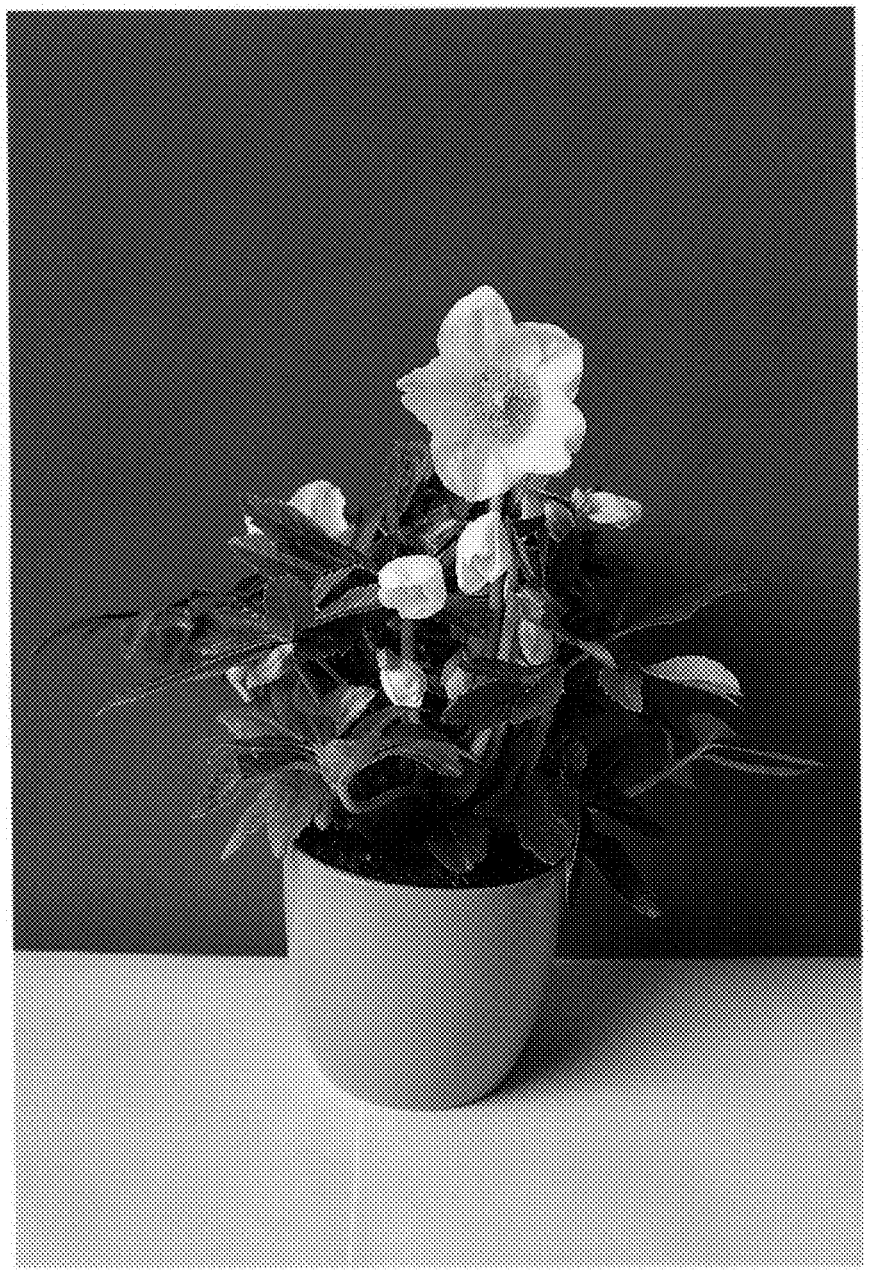

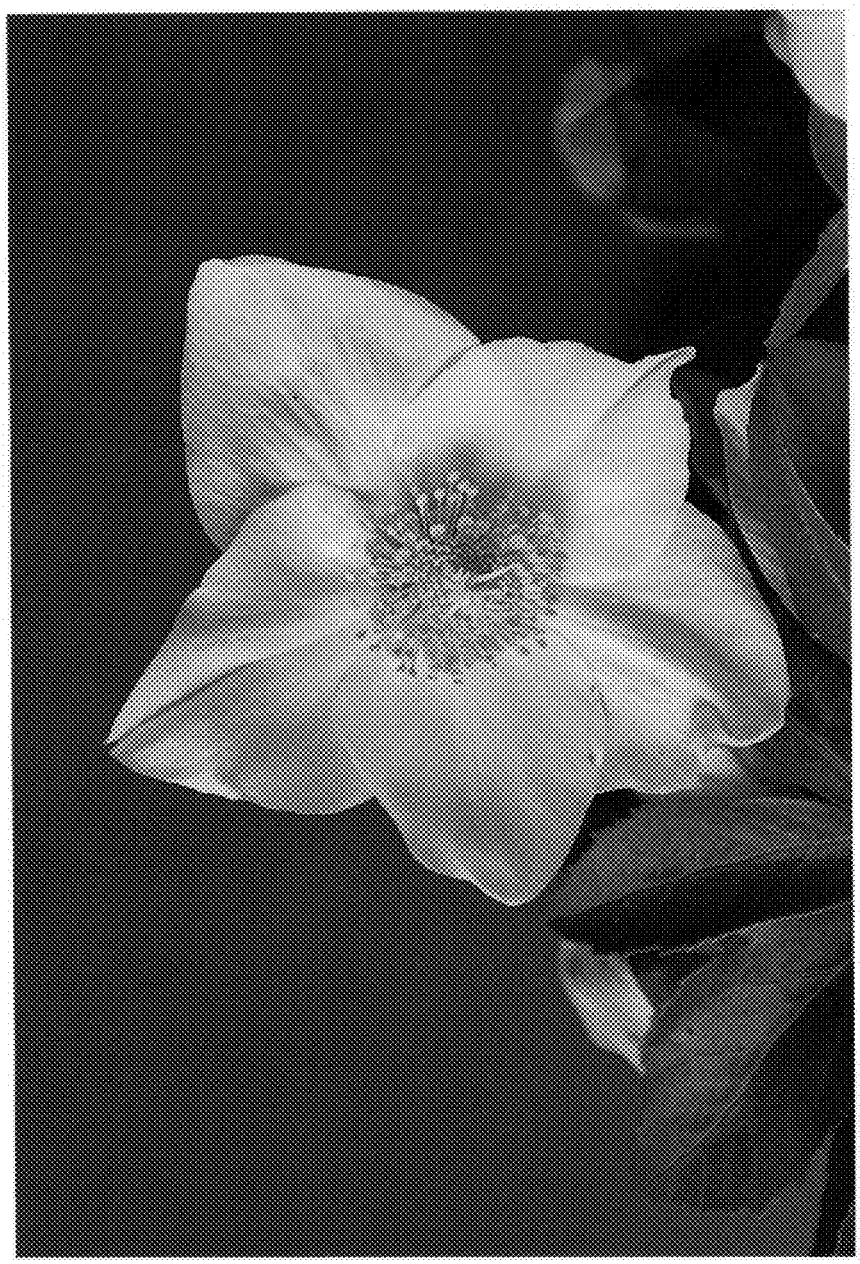

* * * * *